(12) United States Patent
Bergamaschi et al.

(10) Patent No.: US 6,494,206 B1
(45) Date of Patent: Dec. 17, 2002

(54) CUSTOMIZABLE FACE OR NOSE MASK FOR THE NONINVASIVE VENTILATION OF PATIENTS IN GENERAL

(75) Inventors: Paolo Bergamaschi, Concordia (IT); Massimo Fini, Mirandola (IT)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/674,963

(22) PCT Filed: May 11, 1999

(86) PCT No.: PCT/US99/10300
§ 371 (c)(1),
(2), (4) Date: Nov. 3, 2000

(87) PCT Pub. No.: WO99/58198
PCT Pub. Date: Nov. 18, 1999

(30) Foreign Application Priority Data

May 12, 1998 (IT) ........................................ M198A1027

(51) Int. Cl.⁷ ............................................... A62B 18/08
(52) U.S. Cl. ............................... 128/206.24; 128/206.21
(58) Field of Search ........................ 128/206.24, 206.21, 128/206.23, 206.25, 206.26

(56) References Cited

U.S. PATENT DOCUMENTS

| 2,749,910 | A | * | 6/1956 | Faulconer | 128/206.24 |
|---|---|---|---|---|---|
| 2,877,764 | A | * | 3/1959 | Galleher | 1278/206.24 |
| 2,917,045 | A | * | 12/1959 | Schildknecht et al. | 128/206.24 |
| 5,121,745 | A | * | 6/1992 | Israel | 128/202.28 |
| 5,535,736 | A | * | 7/1996 | Jzaw | 128/206.26 |
| 5,592,938 | A | * | 1/1997 | Scarberry et al. | 128/206.24 |
| 5,647,357 | A | * | 7/1997 | Barnett et al. | 128/206.24 |
| 5,832,918 | A | * | 11/1998 | Pantino | 128/205.25 |
| 6,109,263 | A | * | 8/2000 | Feuchtgruber | 128/206.28 |
| 6,152,137 | A | * | 11/2000 | Schwartz et al. | 128/846 |

* cited by examiner

Primary Examiner—Glenn K. Dawson
Assistant Examiner—Joseph F. Weiss, Jr.
(74) Attorney, Agent, or Firm—Fulwider Patton Lee & Utecht, LLP

(57) ABSTRACT

A face mask for the noninvasive ventilation of a patient, the mask being customizable by having a mask body forming at least one surface portion which can be coupled to the face of the patient, the face mask further including at least one chamber containing at least one product without shape memory which can be activated to produce a chemical and/or physical reaction for the transformation of said at least product without shape memory into a body having shape memory which spontaneously models itself on the patient's face at a surface portion between the mask and the patient's face.

8 Claims, 1 Drawing Sheet

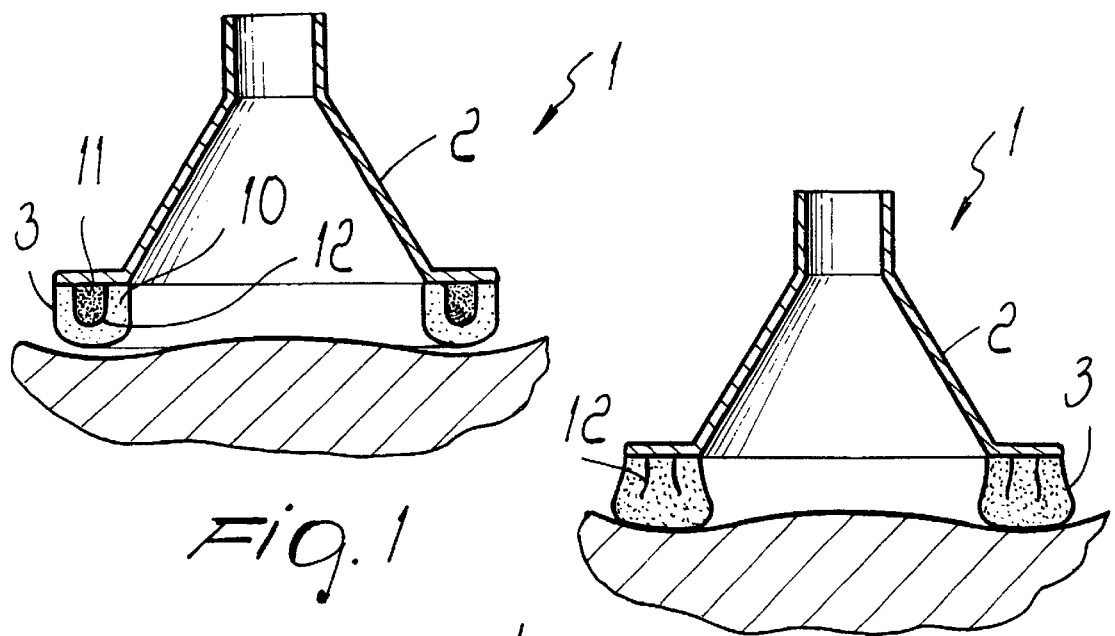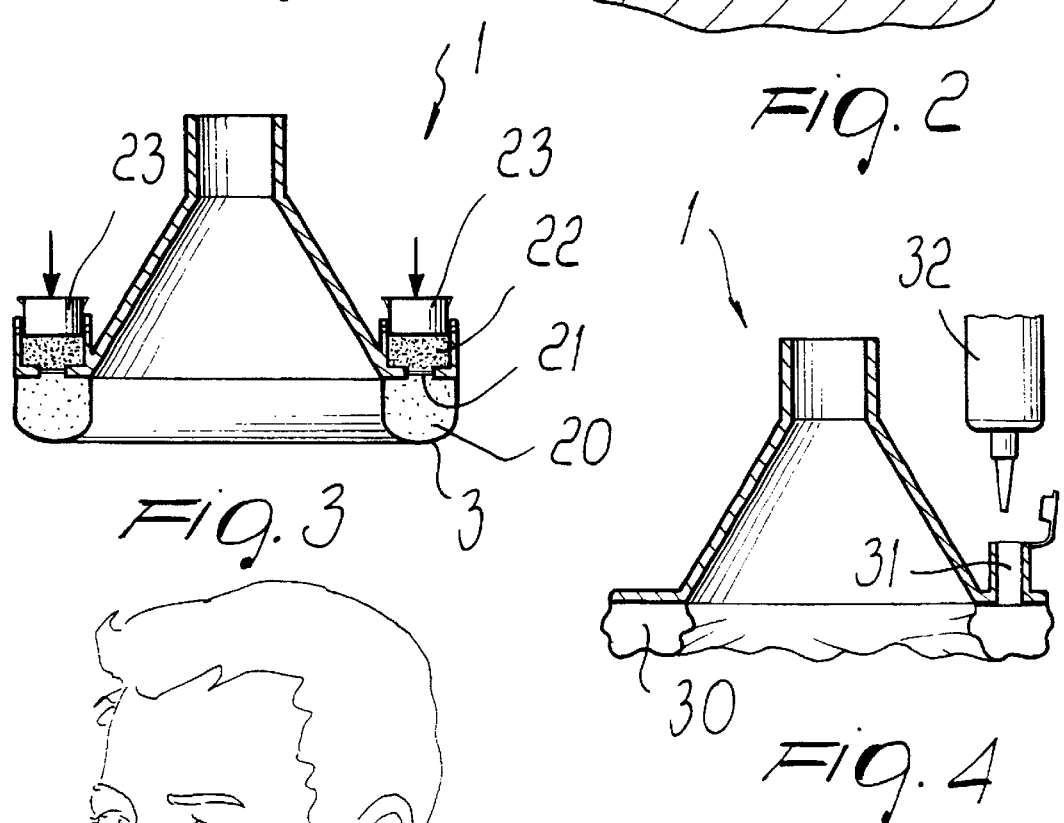

CUSTOMIZABLE FACE OR NOSE MASK FOR THE NONINVASIVE VENTILATION OF PATIENTS IN GENERAL

The present invention relates to a customizable face or nose mask for the noninvasive ventilation of patients in general.

It is known that the noninvasive ventilation of patients in general is based on the use of a face or nose mask which is applied by exerting a positive pressure so as to provide the intended seal at the perimetric edges of the mask in contact with the patient's face.

One of the most severe problems to be overcome is the patient's tolerance of the machine-face interface, which is constituted by the mask proper.

Due to the considerable anatomical diversity of faces, it is necessary to apply a certain force to the mask in order to ensure its tightness; accordingly, though using of very soft materials, in the long term the pressure on the face leads to more or less severe traumas for the patient.

Markedly better results have been achieved by using masks which are produced starting from a mold formed on the patient's face; essentially, a mold of the patient's face is made and a relatively soft material, generally silicone, is then poured onto said mold; the material assumes the anatomical shape of the patient's face and accordingly minimal pressure is sufficient to provide the intended seal against the face.

Although these embodiments are valid from a functional point of view, they suffer the severe drawback of having an exceptionally high cost, since it is necessary to provide a specific mold to form the mask in each individual case.

These solutions furthermore require relatively long production times; together with their high costs, these factors have led to a limited diffusion of these types of mask.

The aim of the invention is to provide a customizable face or nose mask for the noninvasive ventilation of patients in general, which can be modeled directly on the individual patient without thereby requiring the making of a mold.

Within the scope of this aim, a particular object of the invention is to provide a customizable mask in which it is possible to perform adaptation to the individual patient in a very short time without having to resort to special devices.

Another object of the present invention is to provide a customizable mask which, by way of its particular constructive features, is capable of giving the greatest assurances of reliability and safety in use.

Another object of the present invention is to provide a customizable mask which can be easily obtained starting from commonly commercially available elements and materials and is also inexpensive, thus contributing to the diffusion of the mask among users.

This aim, these objects and others which will become apparent hereinafter are achieved by a customizable face or nose mask for the noninvasive ventilation of patients in general, which comprises a mask body forming at least one surface portion which can be coupled to the face of the patient, characterized in that it comprises, at least at said surface portion, a chamber for containing at least one product without shape memory which can be activated to produce a chemical and/or physical reaction for the transformation of said at least one product without shape memory into a product having shape memory which spontaneously models itself on the patient's face.

Further characteristics and advantages of the present invention will become apparent from the description of some preferred but not exclusive embodiments, illustrated only by way of non-limitative example in the accompanying drawings, wherein:

FIG. 1 is a schematic sectional view of a customizable mask with two separate containers for two products which can be mixed to provide a material without shape memory;

FIG. 2 is a schematic view of the step for the self-modeling of the mask;

FIG. 3 is a schematic view of the mask with the two components of the reaction provided in two separate regions;

FIG. 4 is a schematic sectional view of the mask in which it is possible to introduce a self-modeling material;

FIG. 5 is a schematic view of the mask applied to a patient.

With reference to the above figures, the customizable face or nose mask for the noninvasive ventilation of patients in general, generally designated by the reference numeral 1, comprises a mask body 2 which has at least one surface portion 3 which can be coupled to the face of the patient.

The surface portion is preferably provided by a flexible element which internally delimits a region or chamber containing at least one product without shape memory.

In greater detail, it is possible to provide different embodiments, and in particular the chamber, as shown in the examples of FIGS. 1 and 2, is constituted by a first region 10 and by a second region 11 which are separated one another by a breakable membrane 12.

The first region 10 and the second region 11 contain a first product and a second product which, when the breakable membrane 12 is broken, react together, producing a product having shape memory which self-models on the face of the patient.

In the embodiment shown in FIG. 3, the chamber is provided by means of a first container 20 which is separated, by means of a breakable partition 21, from at least one second container 22 on which there acts a plunger 23 for pushing the second component, which can be introduced in the first container 20, where there is a first component which reacts chemically so as to obtain a product having shape memory.

According to FIG. 4, a chamber 30 is provided which is delimited by the flexible plate-like element 3 forming the surface portion for coupling to the face of the patient and which is equipped with an inlet 31 in which it is possible to couple a nozzle for introducing a component or binary component, in the form of foam or in another form, which reacts directly inside the chamber 30, providing a product having shape memory which self-models on the face of the patient.

Essentially, the material or binary materials, by setting, assume the shape of the container, which is delimited in practice by the flexible sheet-like element which, in contact with the face of the patient, shapes the product so as to provide a truly customized mask.

Once the chemical or physical reaction has occurred, the hardness of the material is not very important in itself, since it is possible to use both a rigid material, by providing soft sealing elements on the flexible sheet-like element, and a soft material, which directly acts as a gasket.

Usable materials belong to a wide range;

in particular, it is possible to use all materials which can lead to a chemical or physical reaction which alters their state from fluid without memory, or in any case from a material having no shape of its own, into a solid or gel which has memory, i.e., can resume its own shape.

Merely by way of example, mention is made of polyurethanes, which assume the intended shape when the two components are mixed, gelled water-soluble polyurethanes, foams, and so forth.

When the reaction occurs, the temperature during setting should not exceed 40° C. in view of the fact that said setting occurs in contact with the skin.

Moreover, the recommendable duration of the setting process must be on the order of no more than 5–10 minutes, since this is considered to be an acceptable time for which the patient can keep the mask on his face without moving it during the reaction of the components.

From the above description it is thus clear that the invention achieves the intended aim and objects; in particular, it is stressed that a customizable mask is provided which can be shaped directly in contact with the patient's face without having to resort to all the complicated operations which are typical of the solutions of the prior art.

The invention thus conceived is susceptible of numerous modifications and variations, all of which are within the scope of the inventive concept.

All the details may furthermore be replaced with other technically equivalent elements.

In practice, the materials employed, as well as the contingent shapes and dimensions, may be any according to requirements.

What is claimed is:

1. A customizable face or nose mask for noninvasive ventilation of patients in general, which comprises a mask body forming at least one surface portion which can be coupled to a patient's, said mask body further comprises, at least at said surface portion, a chamber for containing at least one product without shape memory which can be activated to produce a chemical or physical reaction for transformation of said at least one product without shape memory into a solid or gel product having shape memory which spontaneously models to the patient's face, and wherein said containment chamber comprises a first region and a second region which are mutually separated from one another by a breakable membrane, said first region and said second region respectively containing a first product and a second product which mutually react to obtain said solid or gel product having shape memory.

2. The mask according to claim 1, characterized in that said surface portion that can be coupled to the face of the patient is constituted by a flexible element.

3. The mask according to claim 1, characterized in that said chamber comprises a first container which is separated, by means of the breakable membrane, from a second container in which there acts a plunger for pushing acts upon the second product which is suitable to react with the first product provided in said first container.

4. The mask according to claim 1, characterized in that the reaction occurs at a temperature which is equal to, or lower than, 40° C.

5. The mask according to claim 1, characterized in that reaction time of said at least one product for transformation from said product without shape memory into said solid or gel product having shape memory is shorter than 10 minutes.

6. A customizable face or nose mask for noninvasive ventilation of patients in general, which comprises a mask body forming at least one flexible element which can be coupled to patient's face, comprising:

a chamber at least at said surface portion for containing at least one product without shape memory which can be activated to produce a chemical or physical reaction for transformation of said at least one product without shape memory into a solid or gel product having shape memory which spontaneously models to the patient's face, and wherein said containment chamber is delimited by said flexible element and has an inlet for introducing a product that is suitable to react, when the product is introduced in said chamber, so as to obtain said solid or gel product having shape memory.

7. The mask according to claim 6, characterized in that the reaction occurs at a temperature which is equal to, or lower than, 40° C.

8. The mask according to claim 6, characterized in that reaction time of said at least one product for transformation from said product without shape memory into said solid or gel product having shape memory is shorter than 10 minutes.

* * * * *

UNITED STATES PATENT AND TRADEMARK OFFICE
CERTIFICATE OF CORRECTION

PATENT NO. : 6,494,206 B1  
DATED : December 17, 2002  
INVENTOR(S) : Paolo Bergamaschi et al.

It is certified that error appears in the above-identified patent and that said Letters Patent is hereby corrected as shown below:

<u>Title page,</u>  
Item [56], References Cited, add -- FOREIGN PATENTS DOCUMENTS  
-- EP  0  564 361 A1  10/1993  
    EP  0  151 876    8/1985  
    DE  85  13250    8/1985  
    DE  0  332 676    1/1974  
    DE  2  306 251    8/1973  
    DE  1  039 419    9/1958  
    DE  1  023 704    1/1958 --.

<u>Column 3</u>  
Line 29, after "patient's", add -- face --.

<u>Column 4</u>  
Line 7, after "which", delete "there acts".  
Line 21, after "to", add -- a --.

Signed and Sealed this

Sixth Day of May, 2003

JAMES E. ROGAN  
*Director of the United States Patent and Trademark Office*